(12) United States Patent
Lin et al.

(10) Patent No.: US 12,408,989 B2
(45) Date of Patent: *Sep. 9, 2025

(54) METHOD AND SYSTEM FOR SURGICAL NAVIGATION

(71) Applicant: Remex Medical Corp., Taichung (TW)

(72) Inventors: Chen-Tai Lin, Taichung (TW);
Shan-Chien Cheng, Taichung (TW);
Ying-Yi Cheng, Taichung (TW)

(73) Assignee: Remex Medical Corp., Taichung (TW)

( * ) Notice: Subject to any disclaimer, the term of this patent is extended or adjusted under 35 U.S.C. 154(b) by 431 days.

This patent is subject to a terminal disclaimer.

(21) Appl. No.: 18/047,268

(22) Filed: Oct. 17, 2022

(65) Prior Publication Data

US 2023/0115934 A1    Apr. 13, 2023

Related U.S. Application Data

(63) Continuation-in-part of application No. 17/389,747, filed on Jul. 30, 2021, now Pat. No. 11,832,897.

(51) Int. Cl.
*A61B 34/20* (2016.01)
*A61B 90/00* (2016.01)

(52) U.S. Cl.
CPC .............. *A61B 34/20* (2016.02); *A61B 90/36* (2016.02); *A61B 2034/2055* (2016.02); *A61B 2090/364* (2016.02)

(58) Field of Classification Search
None
See application file for complete search history.

(56) References Cited

U.S. PATENT DOCUMENTS

2017/0258526 A1* 9/2017 Lang ................... A61B 17/1742
2021/0113239 A1* 4/2021 Donovan ........... A61B 18/1482
2021/0386556 A1* 12/2021 Betz ..................... A61F 2/30749

* cited by examiner

*Primary Examiner* — Joni Hsu
(74) *Attorney, Agent, or Firm* — CKC & Partners Co., LLC

(57) ABSTRACT

A surgical navigation method includes obtaining a three-dimensional image; selecting a viewing angle direction; generating one or more two-dimensional images arranged along the viewing angle direction from the three-dimensional image; superimposing the one or more two-dimensional images along the viewing angle direction to form a two-dimensional superimposed image; and guiding a movement of a virtual surgical instrument into the two-dimensional superimposed image.

23 Claims, 15 Drawing Sheets

METHOD AND SYSTEM FOR SURGICAL NAVIGATION

RELATED APPLICATIONS

This application is a Continuation-in-part of U.S. application Ser. No. 17/389,747, filed on Jul.30, 2021, now U.S. Pat. No. 11,832,897, issued on Dec. 5, 2023, which is herein incorporated by reference.

BACKGROUND

Technical Field

The present invention generally relates to methods and systems for surgical navigation, and in particular, methods and systems relating to the manipulation of radiographic imagery to provide a more efficient and accurate method for directing surgical tools.

Description of Related Art

Surgical navigational methods and systems help medical staff locate body parts of a patient (such as, e.g., osseous and soft tissue structures) and guide and place medical surgical instruments, and can perform implant placement surgery (such as, e.g., screws, pins, cages, graft materials, etc.) into the body parts. Surgeons may use utilize radiographic images, such as an X-ray scan or a computed tomography (CT) scan, to help locate certain targets in a patient's body. For example, in a case involving the placement of a screw into a patient's spine or a cage into a patient's sacroiliac joint, a surgeon may observe an X-ray image of the patient's spine to help guide the correct placement of the screw. However, there are deficiencies with such conventional surgical navigation systems. For example, whether using X-ray or CT imagery, certain anatomical structures (such as a pedicle on a patient's spine, a sacroiliac joint, etc.) may be difficult to locate, which may lead to extra time in the operating room to correctly place surgical instruments. In turn, extended time in the operating room can lead to complications with anesthesia, a greater risk developing an infection, higher risk for developing a blood clot, and an overall poorer patient outcome. Additionally, difficulty in locating correct anatomical structures may lead to errors in surgical instrument placement. This can result in the need for additional corrective surgeries.

In an attempt to address these deficiencies, surgeons and other medical personnel have resorted to obtaining additional radiographic scans in hopes of obtaining a clearer view of the desired anatomical structure. This approach, however, can be time consuming and result in additional financial costs. Additionally, this approach requires the patient to submit to multiple radiographic scanning procedures, which may harm the patient by increasing the patient's lifetime X-ray exposure (causing an increased risk for developing cancers).

In view of the foregoing, it is desirable to reduce the time and increase the accuracy of identifying anatomical structures in surgical patients. For example, there is a need for an improved method and system to utilize imagery that can more consistently and reliably identify anatomical structures.

SUMMARY

According to one aspect of the present disclosure, a surgical navigation method includes obtaining a three-dimensional image; selecting a viewing angle direction; generating one or more two-dimensional images arranged along the viewing angle direction from the three-dimensional image; superimposing the one or more two-dimensional images along the viewing angle direction to form a two-dimensional superimposed image; and guiding a movement of a virtual surgical instrument into the two-dimensional superimposed image.

According to another aspect of the present disclosure, a surgical navigation system includes a memory, a controller and a display device. The memory is configured to store a three-dimensional image. The controller is configured to select a viewing angle direction according to an instruction; generate one or more two-dimensional images arranged along the viewing angle direction from the three-dimensional image; superimpose the one or more two-dimensional images along the viewing angle direction to form a two-dimensional superimposed image; and guide a virtual surgical instrument into the two-dimensional superimposed image. The display device is configured to display the two-dimensional superimposed image.

According to further another aspect of the present disclosure, a computer-readable storage medium includes instructions, which when executed on a processor causes the processor to perform a surgical navigational method, the surgical navigational method includes obtaining a three-dimensional image; selecting a viewing angle direction according to an instruction; generating one or more two-dimensional images arranged along the viewing angle direction from the three-dimensional image; superimposing the two-dimensional images along the viewing angle direction to form a two-dimensional superimposed image; and guiding a movement of a virtual surgical instrument into the two-dimensional superimposed image.

BRIEF DESCRIPTION OF THE DRAWINGS

The accompanying drawings, which are incorporated in and constitute a part of this disclosure, illustrate various embodiments and aspects of the present disclosure. In the drawings.

DETAILED DESCRIPTION

Figure 1:
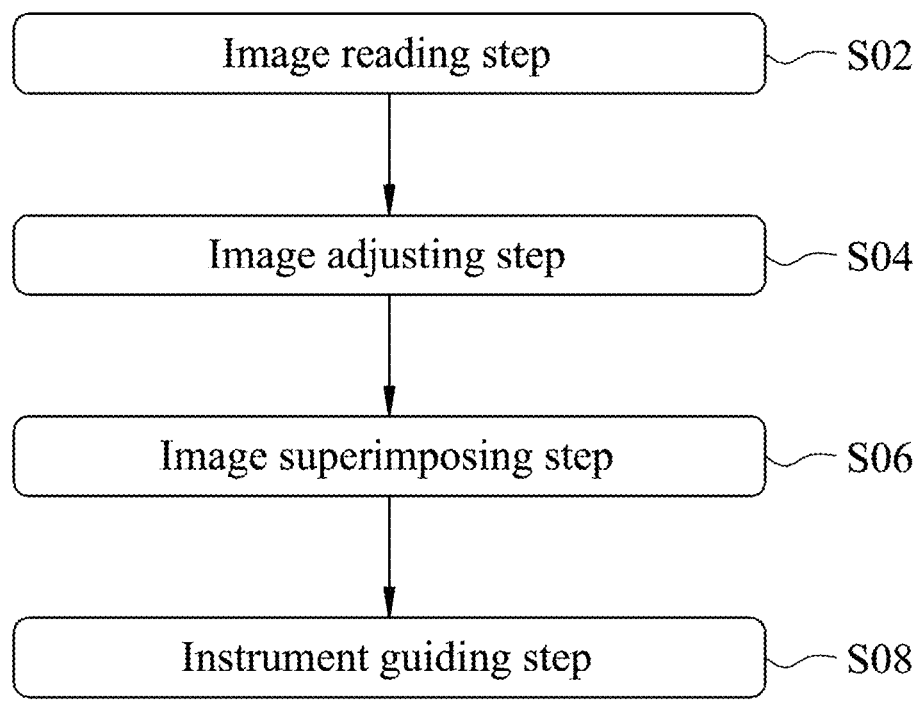
FIG. 1 is a schematic flowchart illustrating a surgical navigation method according to the 1st embodiment of the present disclosure.

The following detailed description refers to the accompanying drawings. Wherever possible, the same reference numbers are used in the drawings and in the following description to refer to the same or similar parts. While several exemplary embodiments and features of the invention are described herein, modifications, adaptations, and other implementations are possible without departing from the spirit and scope of the invention. For example, substitutions, additions, or modifications may be made to the components illustrated in the drawings, and the exemplary methods described herein may be modified by substituting, reordering, or adding steps to the disclosed methods. Accordingly, the following detailed description does not limit the invention. Instead, the proper scope of the invention is defined by the appended claims.

In addition, when a component (or apparatus or module, etc.) is "connected/linked to" another component, it may mean that the component is directly connected/linked to the another component, or it may mean that a certain component is indirectly connected/linked to another component, i.e., there are other components between the component and the another component. When it is clearly stated that a certain component is "directly connected/linked" to another component, it means that there is no other component between the component and the another component. The terms "first", "second", "third", etc. are only used to describe different components, and there are no restrictions on the components themselves. Therefore, the first component may also be renamed the second component. In addition, a combination of components/apparatuses/circuits herein is not a commonly known, conventional or well-known combination in the art. Whether components/units/circuits themselves are well-known cannot be used to determine whether the combination relationship thereof is easily completed by a person of ordinary skill in the art.

FIG. 1 is a schematic flowchart illustrating a surgical navigation method 100 according to the 1st embodiment of the present disclosure. The surgical navigation method 100 is used for guiding a virtual surgical instrument and includes an image reading step S02, an image adjusting step S04, an image superimposing step S06, and an instrument guiding step S08.

In accordance with some embodiments of the present disclosure, the image reading step S02 includes reading a three-dimensional image (such as, e.g., an image of a spine), from a memory. The three-dimensional image includes one or more two-dimensional images, and the two-dimensional images may be obtained through scanning along at least one cutting direction. In accordance with some embodiments, the image adjusting step S04 includes selecting a part or portion of one or more of the selected two-dimensional spinal images along at least one viewing angle direction, where the part of the two-dimensional spinal images contains a three-dimensional pedicle region.

In accordance with some embodiments of the present disclosure, the image superimposing step S06 includes superimposing the selected part of the two-dimensional spinal images (along the at least one viewing angle direction) to form a superimposed viewing direction image. The superimposed viewing direction image presents at least one two-dimensional superimposed region according to the at least one viewing angle direction, and the at least one two-dimensional superimposed region corresponds to the three-dimensional pedicle region.

In accordance with some embodiments of the present disclosure, the instrument guiding step S08 includes real time rendering the virtual surgical instrument in the at least one two-dimensional superimposed region of the superimposed viewing direction image according to the position of the surgical instrument. Therefore, according to the surgical navigation method 100, two-dimensional spinal images are superimposed and presented in a specific range. In accordance with some embodiments, utilizing this superimposed viewing direction image helps distinguish a pedicle contour because the outer layer of the pedicle is of high density bone and high density bone appears bright white in the image. Depending on the viewing angle direction chosen, a coronal plane contour, a sagittal plane contour or an axial plane contour of pedicle can be clearly identified in the image allowing for efficient application of a CBT screw implantation technique. Medical staff may correctly fix a screw in the pedicle using the superimposed viewing direction image and can greatly shorten the time for medical staff to find and determine an implantation position and path, thereby improving safety and patient outcomes. The following description provides detailed embodiments to illustrate the details of the above steps.

Figure 2:
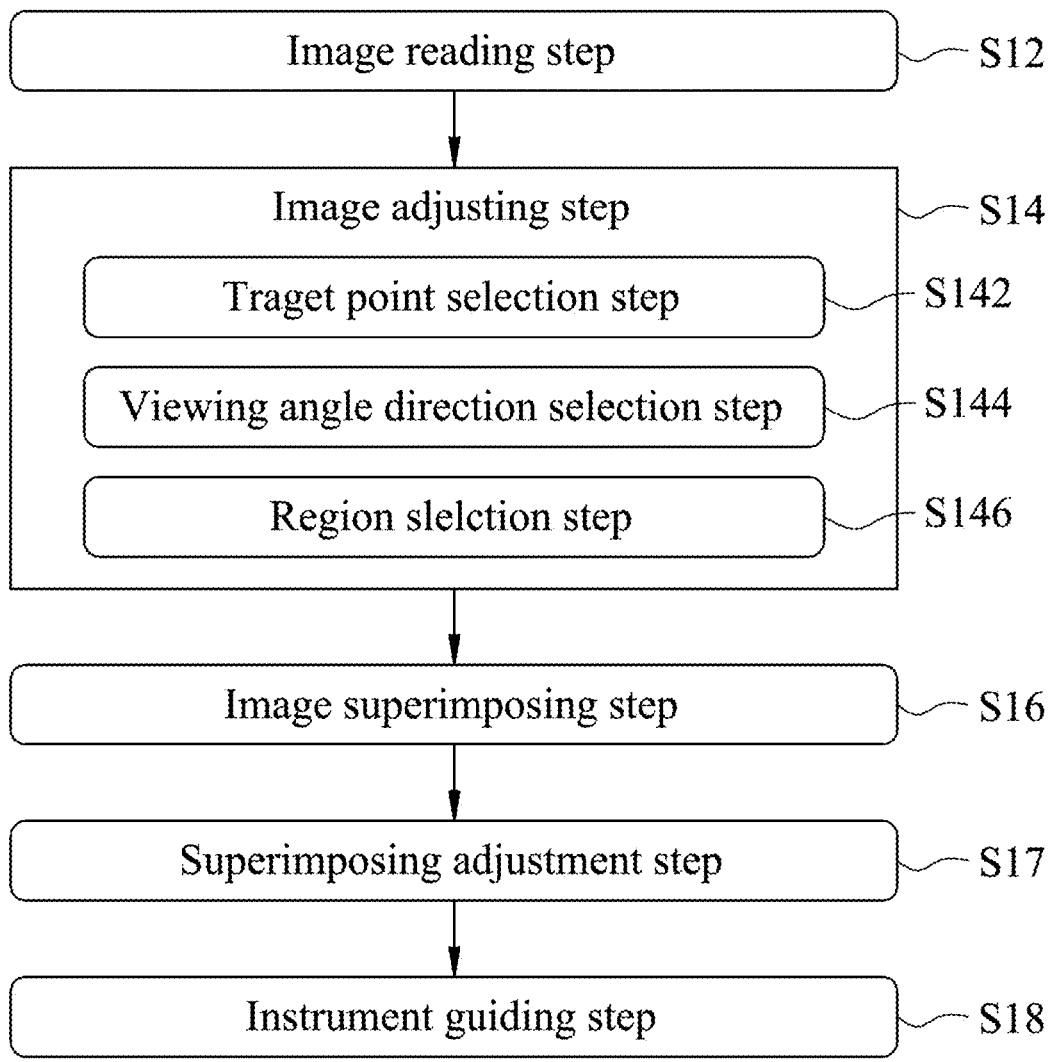
FIG. 2 is a schematic flowchart illustrating a surgical navigation method according to the 2nd embodiment of the present disclosure.
Figure 3:
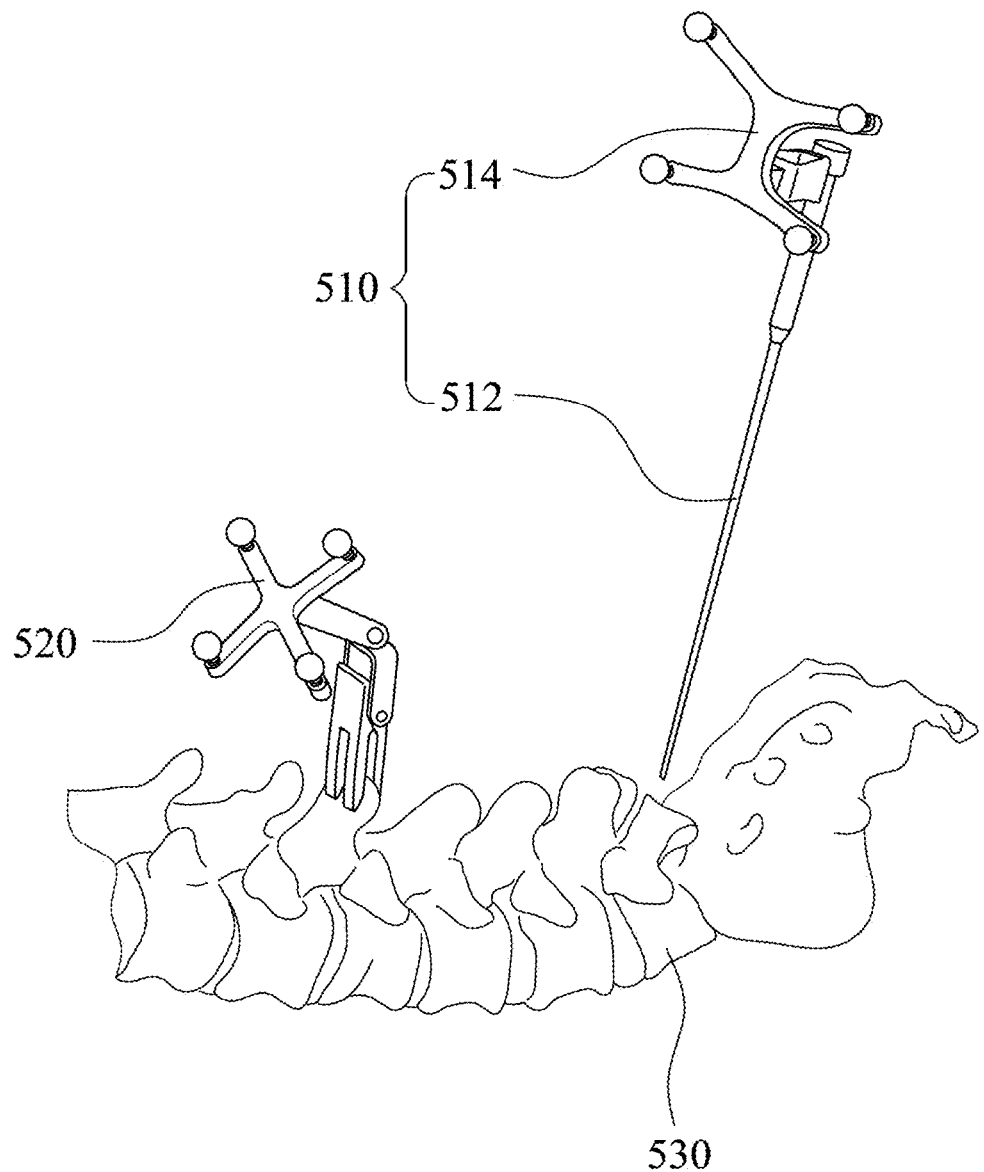
FIG. 3 is a schematic diagram illustrating the guiding of a virtual surgical instrument using the surgical navigation method of FIG. 2.
Figure 4:
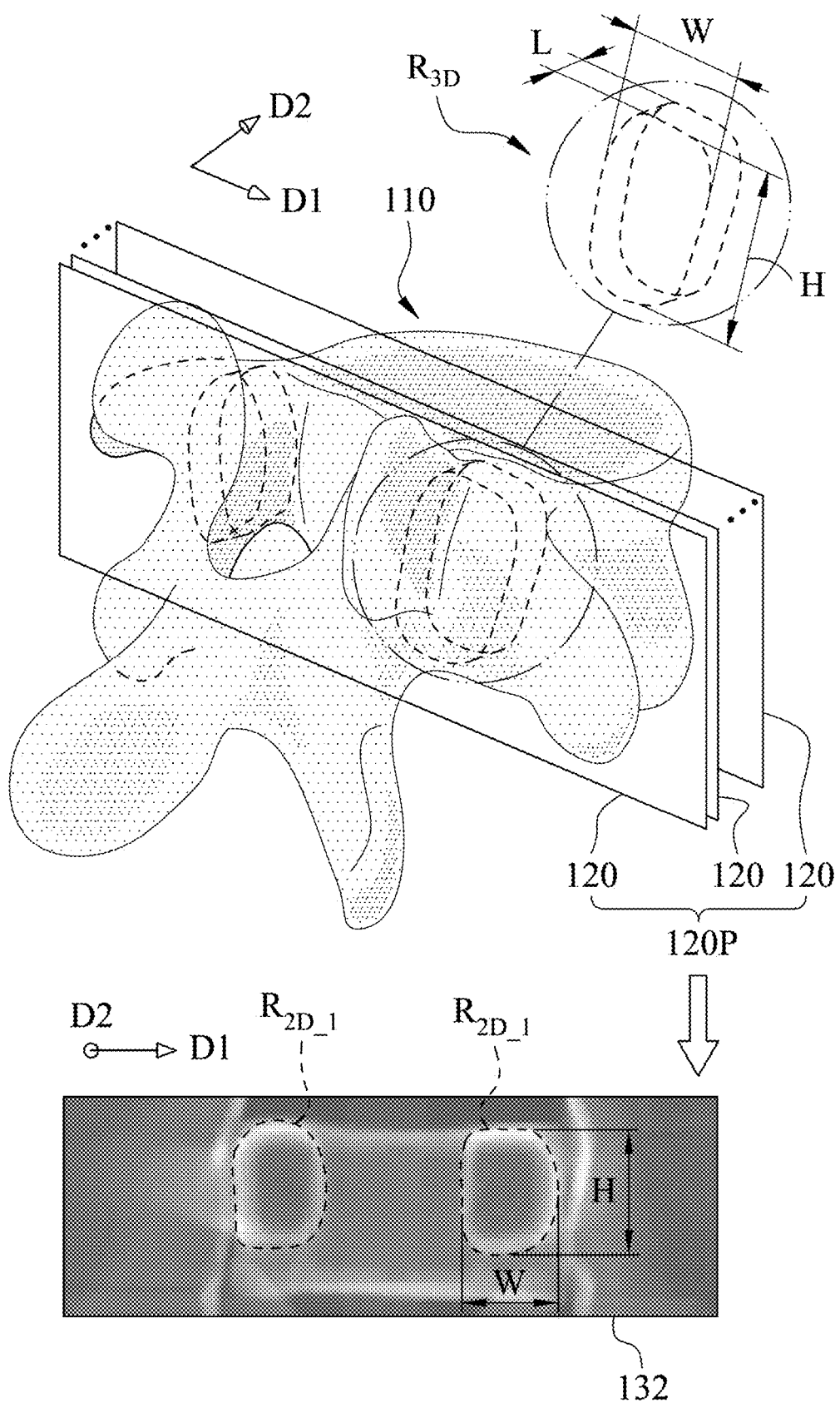
FIG. 4 is a schematic diagram illustrating superimposition at a spinal segment location corresponding to an image superimposing step of the surgical navigation method of FIG. 2.
Figure 5:
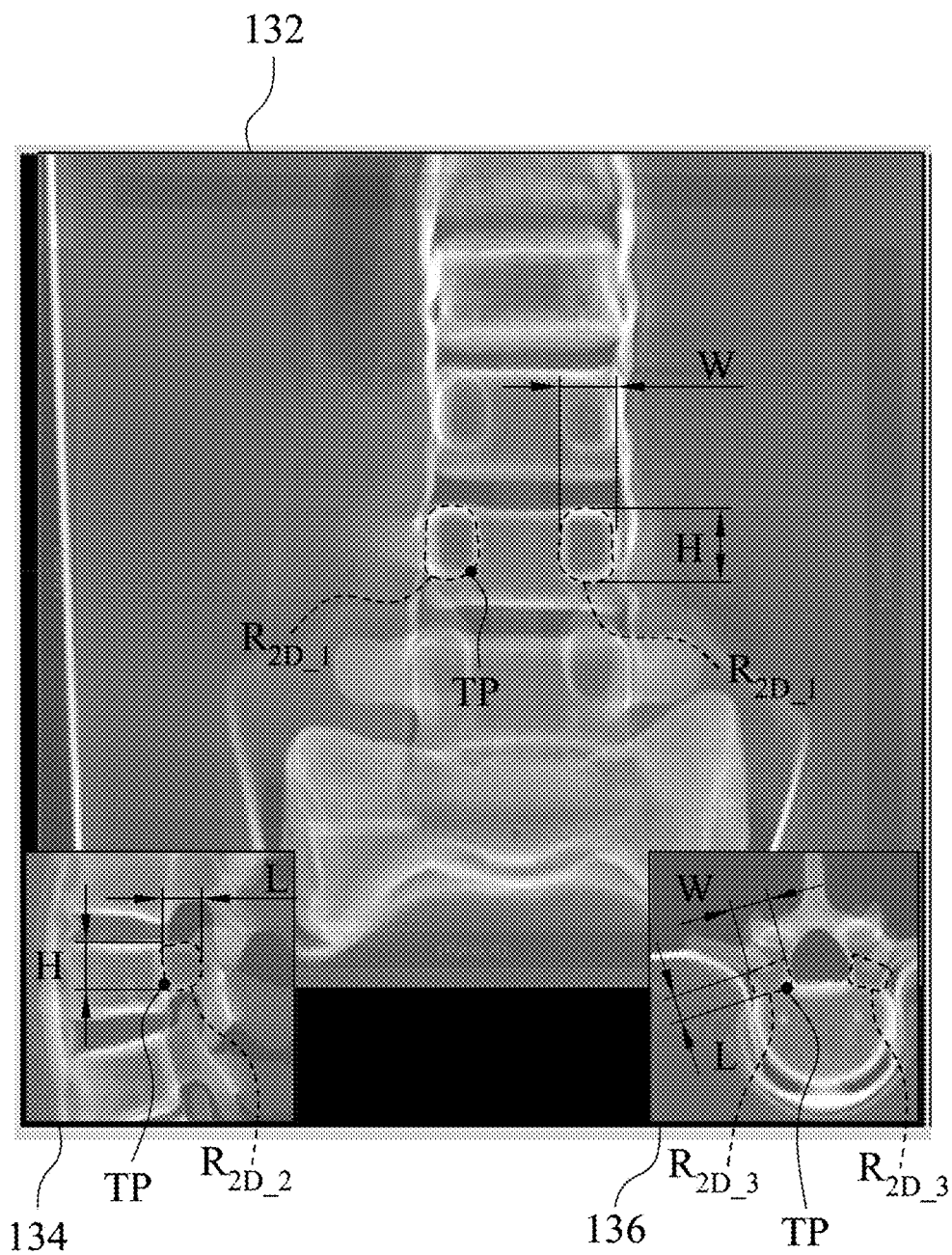
FIG. 5 is a schematic diagram illustrating a superimposed image in a first viewing direction generated in the surgical navigation method of FIG. 2.
Figure 6:
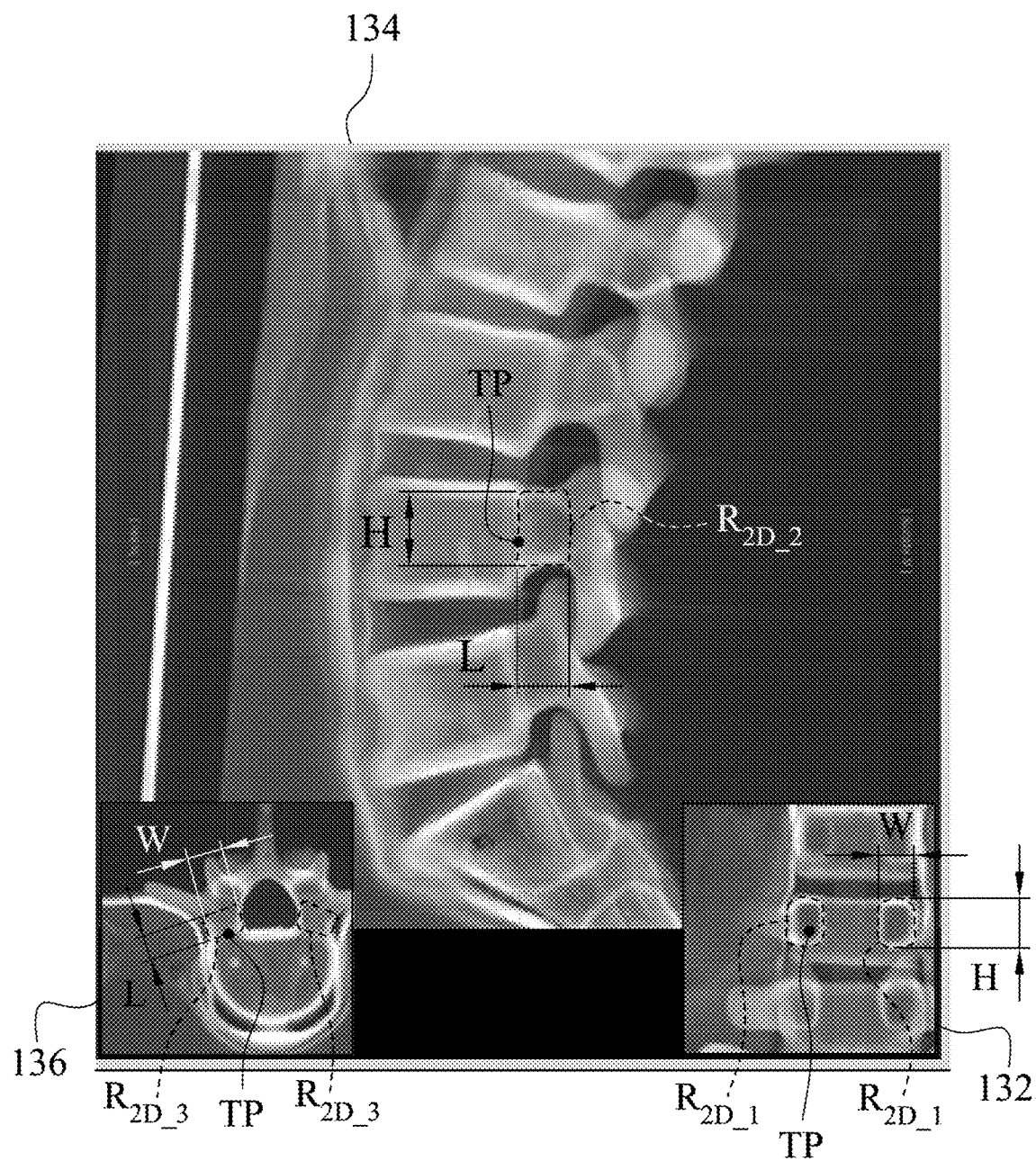
FIG. 6 is a schematic diagram illustrating a superimposed image in a second viewing direction generated in the surgical navigation method of FIG. 2.

FIG. 2 is a schematic flowchart illustrating a surgical navigation method 100a according to the 2nd embodiment of the present disclosure. FIG. 3 is a schematic diagram illustrating the guiding of a surgical instrument 512 by using the surgical navigation method 100a of FIG. 2. FIG. 4 is a schematic diagram illustrating the superimposing at a spinal segment in an image superimposing step S16 of the surgical navigation method 100a of FIG. 2. FIG. 5 is a schematic diagram illustrating a superimposed viewing direction image 130 of the surgical navigation method 100a of FIG. 2. FIG. 6 is a schematic diagram illustrating another superimposed viewing direction image 130a of the surgical navigation method 100a of FIG. 2.

In accordance with some embodiments of the present disclosure, the surgical navigation method 100a is used for guiding a virtual surgical instrument. The virtual surgical instrument may correspond to one surgical instrument 512 and may be displayed for the surgeon. The surgical navigation method 100a includes an image reading step S12, an image adjusting step S14, an image superimposing step S16, a superimposing adjustment step S17, and an instrument guiding step S18. In accordance with some embodiments, the image reading step S12, the image adjusting step S14, the image superimposing step S16, the superimposing adjustment step S17, and the instrument guiding step S18 may be applied in conjunction with a cortical bone trajectory (CBT) screw implantation technique where the virtual surgical instrument is a virtual screw, and the surgical instrument 512 is a screw. However, other virtual surgical instruments and surgical instruments 512 may be used.

In accordance with some embodiments of the present disclosure, the image reading step S12 includes reading a three-dimensional spinal image 110 from a memory, where the three-dimensional spinal image 110 includes two-dimensional spinal images 120, and the two-dimensional spinal images 120 are obtained through scanning along at least one cutting direction D1. In accordance with some embodiments, the three-dimensional spinal image 110 is a three-dimensional medical image generated through scanning of the spine by CT and reconstruction. During CT scanning, specific scanning parameters are used to obtain a required image. The scanning parameters include a layer thickness and a spacing, where the layer thickness denotes a section thickness of each two-dimensional spinal image 120, and the spacing denotes a distance between two adjacent two-dimensional spinal images 120. In other words, each two-dimensional spinal image 120 has a layer thickness, and there is a spacing between adjacent two of the two-dimensional spinal images 120.

In accordance with some embodiments of the present disclosure, the image adjusting step S14 includes selecting a part 120P of one or more of the two-dimensional spinal images 120 along at least one viewing angle direction D2, where the part 120P of the one or more two-dimensional spinal images 120 contains a three-dimensional pedicle region $R_{3D}$. In accordance with some embodiments, the image adjusting step S14 includes a target point selection step S142, a viewing angle direction selection step S144, and a region selection step S146, where the target point selection step S142 includes selecting a target point TP from the two-dimensional spinal images 120. The viewing angle direction selection step S144 includes selecting the at least one viewing angle direction D2 according to the two-dimensional spinal images 120. The region selection step S146 is to select the part 120P of the two-dimensional spinal images 120 along the at least one viewing angle direction D2 for the target point TP of the two-dimensional spinal images 120, where the part 120P of the two-dimensional spinal images 120 contains a three-dimensional pedicle region $R_{3D}$. Furthermore, the three-dimensional pedicle region $R_{3D}$ is columnar and has a pedicle length L, a pedicle width W, and a pedicle height H. The target point TP is close to the three-dimensional pedicle region $R_{3D}$.

In accordance with some embodiments of the present disclosure, the image superimposing step S16 includes superimposing the part 120P of the two-dimensional spinal images 120 along the at least one viewing angle direction D2 to form a superimposed viewing direction image 130, where the superimposed viewing direction image 130 presents at least one two-dimensional superimposed region (such as $R_{2D\_1}$ in FIG. 4 and $R_{2D\_1}$, $R_{2D\_2}$ and $R_{2D\_3}$ in FIGS. 5 and 6) according to the at least one viewing angle direction D2, and the at least one two-dimensional superimposed region corresponds to the three-dimensional pedicle region $R_{3D}$.

In accordance with embodiments of the present disclosure, the image superimposing step S16 is advantageous because high bone density regions appear white in a CT image, and because the pedicle surface density is high. Thus, the two-dimensional superimposed region corresponding to the three-dimensional pedicle region $R_{3D}$ can clearly identify the white pedicle contour in the picture. Additionally, different viewing angle directions D2, may generate different superimposed viewing direction images 130 and corresponding two-dimensional superimposed regions, such as a coronal plane contour, a sagittal plane contour or an axial plane contour of pedicle. In accordance with some embodiments, the number of the viewing angle directions D2 is the same as that of the two-dimensional superimposed regions and the number may be plural, and the viewing angle directions D2 may include (but not limited to) a first viewing angle direction, a second viewing angle direction, and a third viewing angle direction. The two-dimensional superimposed regions may include (but not limited to) a first two-dimensional superimposed region $R_{2D\_1}$, a second two-dimensional superimposed region $R_{2D\_2}$, and a third two-dimensional superimposed region $R_{2D\_3}$. The superimposed viewing direction image 130 may include (but not limited to) a superimposed coronal plane 132, a superimposed sagittal plane 134, and a superimposed axial plane 136. The target point TP is close to the first two-dimensional superimposed region $R_{2D\_1}$, the second two-dimensional superimposed region $R_{2D\_2}$, and the third two-dimensional superimposed region $R_{2D\_3}$.

In accordance with some embodiments of the present disclosure, the superimposed coronal plane 132 has a two-dimensional coronal coordinate system, where the superimposed coronal plane 132 presents one or two first two-dimensional superimposed regions $R_{2D\_1}$ according to the three-dimensional pedicle region $R_{3D}$ in the first viewing angle direction, and each first two-dimensional superimposed region R2D_1 has a pedicle height H, a pedicle width W, and a closed contour. The closed contour is the coronal plane contour of pedicle.

In accordance with some embodiments of the present disclosure, the superimposed sagittal plane 134 has a two-dimensional sagittal coordinate system, where the superimposed sagittal plane 134 presents one second two-dimensional superimposed region $R_{2D\_2}$ according to the three-dimensional pedicle region $R_{3D}$ in the second viewing angle direction, and the second two-dimensional superimposed region $R_{2D\_2}$ has a pedicle length L, a pedicle height H, and a sagittal plane contour of pedicle.

In accordance with some embodiments of the present disclosure, the superimposed axial plane 136 has a two-dimensional abscissa system, where the superimposed axial plane 136 presents one or two third two-dimensional superimposed regions $R_{2D\_3}$ according to the three-dimensional pedicle region $R_{3D}$ in the third viewing angle direction, and each third two-dimensional superimposed region $R_{2D\_3}$ has the pedicle length L, the pedicle width W, and an axial plane contour of pedicle. After the image superimposing step S16, the pedicle contour of the spinal segment corresponding to the target point TP in the superimposed viewing direction image 130 is the clearest.

In accordance with some embodiments of the present disclosure, the superimposing adjustment step S17 includes adjusting the number of the parts 120P of the two-dimensional spinal images 120 superimposed along at least one viewing angle direction D2 according to a contour sharpness of the two-dimensional superimposed regions in the superimposed viewing direction image 130.

In accordance with some embodiments of the present disclosure, the instrument guiding step S18 includes real-time rendering the virtual surgical instrument in the two-dimensional superimposed region of the superimposed viewing direction image 130 according to the position of the surgical instrument.

As shown in FIG. 4, in some embodiments, the viewing angle direction D2 of the superimposed coronal plane 132 may be the first viewing angle direction. In accordance with some embodiments, three-dimensional spinal images 110 generated by the CT scanning of one spinal segment along the cutting direction D1 corresponding to the first viewing angle direction include two-dimensional spinal images 120, and the part 120P of these two-dimensional spinal images 120 contains the three-dimensional pedicle region $R_{3D}$.

The two-dimensional spinal images 120 are superimposed to form a superimposed coronal plane 132. The superimposed coronal plane 132 presents one or two first two-dimensional superimposed regions $R_{2D\_1}$ according to the three-dimensional pedicle region $R_{3D}$ in the first viewing angle direction.

In some embodiments, as shown in FIG. 5 and FIG. 6, the viewing angle direction D2 of the superimposed sagittal plane 134 may be the second viewing angle direction. In accordance with some embodiments, three-dimensional spinal images 110 generated by the CT scanning of a plurality of spinal segments along the cutting direction D1 corresponding to the second viewing angle direction include two-dimensional spinal images, and the part of these two-dimensional spinal images covers the three-dimensional pedicle region $R_{3D}$.

The two-dimensional spinal images superimposed along the direction of the pedicle width W (i.e., the second viewing angle direction of the viewing angle direction D2), to form a superimposed sagittal plane 134. The superimposed sagittal plane 134 presents one or two second two-dimensional superimposed region $R_{2D\_2}$ according to the three-dimensional pedicle region $R_{3D}$ in the second viewing angle direction.

In accordance with some embodiments of the present disclosure, as shown in FIG. 5 and FIG. 6, the viewing angle direction D2 of the superimposed axial plane 136 may be the third viewing angle direction. In accordance with some embodiments, three-dimensional spinal images 110 generated by the CT scanning of one spinal segment along the cutting direction D1 corresponding to the third viewing angle direction include two-dimensional spinal images, and the part of these two-dimensional spinal images contains the three-dimensional pedicle region $R_{3D}$.

The two-dimensional spinal images superimposed along the direction of the pedicle height H (i.e., the third viewing angle direction of the viewing angle direction D2), to form a superimposed axial plane 136. The superimposed axial plane 136 presents one or two third two-dimensional superimposed region $R_{2D\_3}$ according to the three-dimensional pedicle region $R_{3D}$ in the third viewing angle direction.

There is no correlation between the operations of adjusting and superimposing images of FIG. 5 and FIG. 6. This means that the adjusting and superimposing images of FIG. 5 and FIG. 6 can be performed independently, such that medical staff can clearly understand the relative positions of the three-dimensional pedicle region $R_{3D}$ in different viewing angles.

In other embodiments, the number, layer thickness T and spacing S of the two-dimensional spinal image 120 of the three-dimensional spinal image 110, and the pedicle length L, pedicle width W, pedicle height H, cutting direction D1, viewing angle direction D2 and position of the target point TP of the three-dimensional pedicle region $R_{3D}$ can be changed according to actual conditions or demands, and the present disclosure is not limited to the above.

In accordance with embodiments of the present disclosure, only the part 120P of the two-dimensional spinal images 120 is superimposed in the present disclosure, which has a clearer local contour, compared with the full display of the two-dimensional spinal images 120 that would otherwise make it harder to focus on the point of interest.

Figure 7:
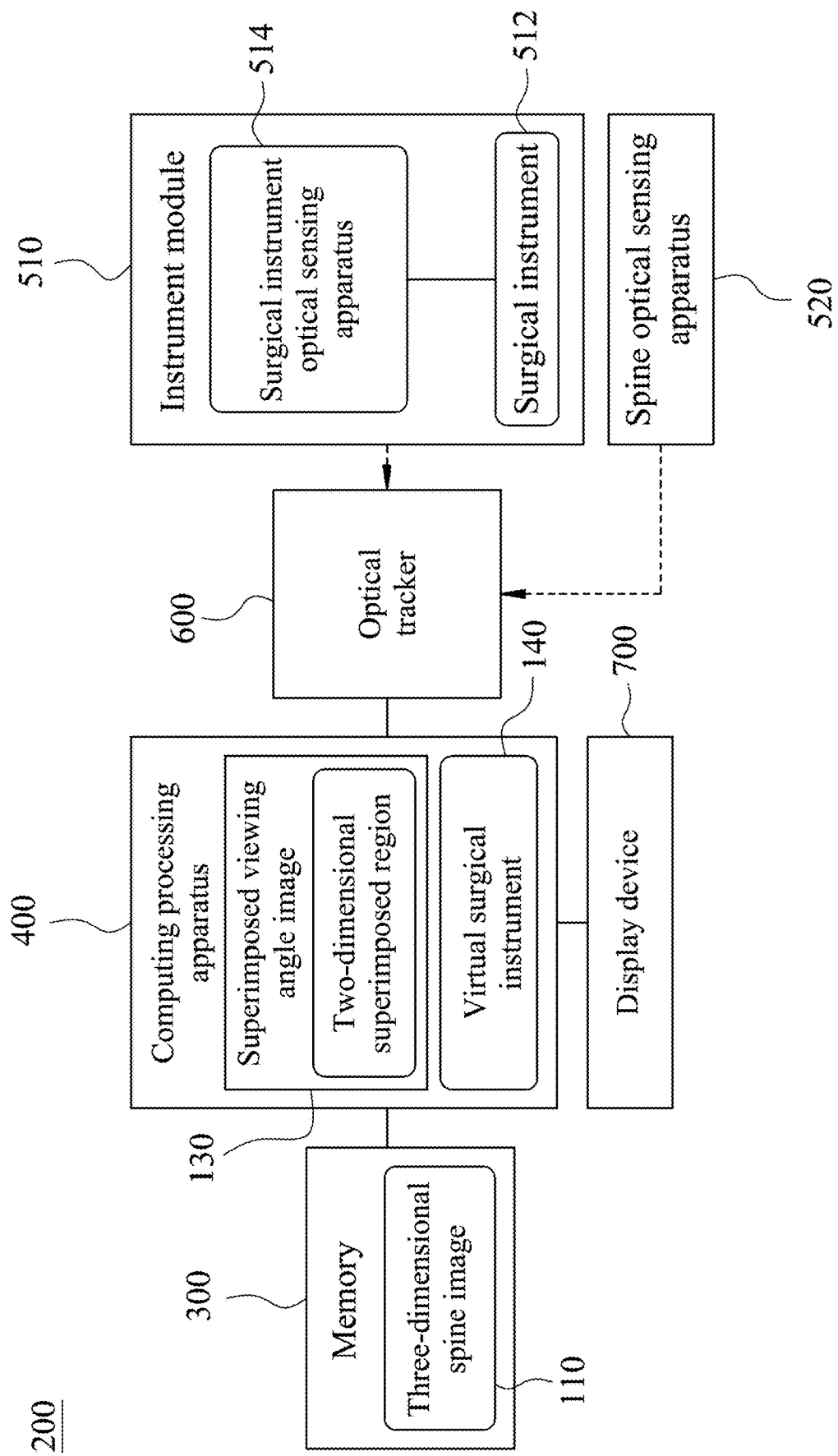
FIG. 7 is a schematic diagram illustrating a surgical navigation system according to the 3rd embodiment of the present disclosure.

FIG. 7 is a schematic diagram illustrating a surgical navigation system 200 according to the 3rd embodiment of the present disclosure. The surgical navigation system 200 is configured to guide a virtual surgical instrument 140 and includes a memory 300, a processor 400, an instrument module 510, a spine optical sensing apparatus 520, an optical tracker 600, and a display device 700.

Although not shown, the various components of surgical navigation system 200 need not be fully contained within the user device. Each of the components may be physically separated from another and more than one of the components may be used to perform methods consistent with the present disclosure. Even though the components may be physically separated, the components may still be communicably connected by means of wired or wireless technology. For example, different components of system 100 and user device may be connected through the Internet, a LAN (local area network), a WAN (wide area network), databases, servers, RF (radio frequency) signals, cellular technology, Ethernet, telephone, "TCP/IP" (transmission control protocol/internet protocol), and any other electronic communication format.

In accordance with some embodiments of the present disclosure, the memory 300 is configured to access a three-dimensional spinal image 110, where the three-dimensional spinal image 110 includes one or more two-dimensional spinal images 120, and the two-dimensional spinal images 120 are obtained through scanning along at least one cutting direction D1. The memory 300 may include all forms of computer-readable storage mediums such as non-volatile or volatile memories including, by way of example, semiconductor memory devices, such as EPROM, RAM, ROM, DRAM, EEPROM, and flash memory devices; magnetic disks such as internal hard disks and removable disks; magneto-optical disks; DVD disks, and CD-ROM disks. Memory device 300 may be used to store program code.

In accordance with some embodiments of the present disclosure, the processor 400 is electrically connected to the memory 300, where the computing processing apparatus 400 receives the three-dimensional spinal image 110 and is configured to perform operations including the following steps: an image reading step S02/S12, an image adjusting step S04/S14, an image superimposing step S06/S16, a superimposing adjustment step S17, and an instrument guiding step S08/S18 described above and shown in FIG. 1 to FIG. 6.

In accordance with some embodiments of the present disclosure, the processor 400 may be an ASIC (Application Specific Integrated Circuit) or it may be a general purpose processor. The processor 400 may include more than one processor. For example, processors may be situated in parallel, series, or both in order to process all or part of the computer instructions that are to be processed.

In accordance with some embodiments of the present disclosure, the instrument module 510 includes a surgical instrument 512 and a surgical instrument optical sensing apparatus 514, where the surgical instrument 512 is controlled and displaced by medical staff. The surgical instrument optical sensing apparatus 514 may be disposed on the surgical instrument 512, and includes a reflective ball and a fixing frame, and the fixing frame may be located between the reflective ball and the surgical instrument 512. The surgical instrument 512 may be a CBT screw, a guide probe or another surgical instrument, depending on the selection of medical staff and use conditions. The spine optical sensing apparatus 520 may be disposed on a spine 530 and includes a reflective ball and a fixing frame. The fixing frame may be located between the reflective ball and the spine 530. The optical tracker 600 may be electrically connected to the processor 400 and configured to track the spine 530 and the surgical instrument 512. When the medical staff control the surgical instrument 512, the surgical instrument optical sensing apparatus 514 may be facing to the optical tracker 600, so that the optical tracker 600 can track the surgical instrument 512 in real time. In addition, the spine optical sensing apparatus 520 may also be facing to the optical tracker 600, so that the optical tracker 600 can track the spine 530 in real time.

In accordance with some embodiments of the present disclosure, the display device 700 may be electrically connected to the processor 400, and displays a screen picture, and the screen picture presents the superimposed coronal plane 132, the superimposed sagittal plane 134, the superimposed axial plane 136 or the virtual surgical instrument 140 of the superimposed viewing direction image 130/130a. The display device 700 may be any conventional user interface display device. For example, display device 700 may include computer monitors, televisions, and LCD displays. Display device 700 may display GUI (Graphical User Interface) which allows a user to interact with system 200 hardware and software applications.

Figure 8:
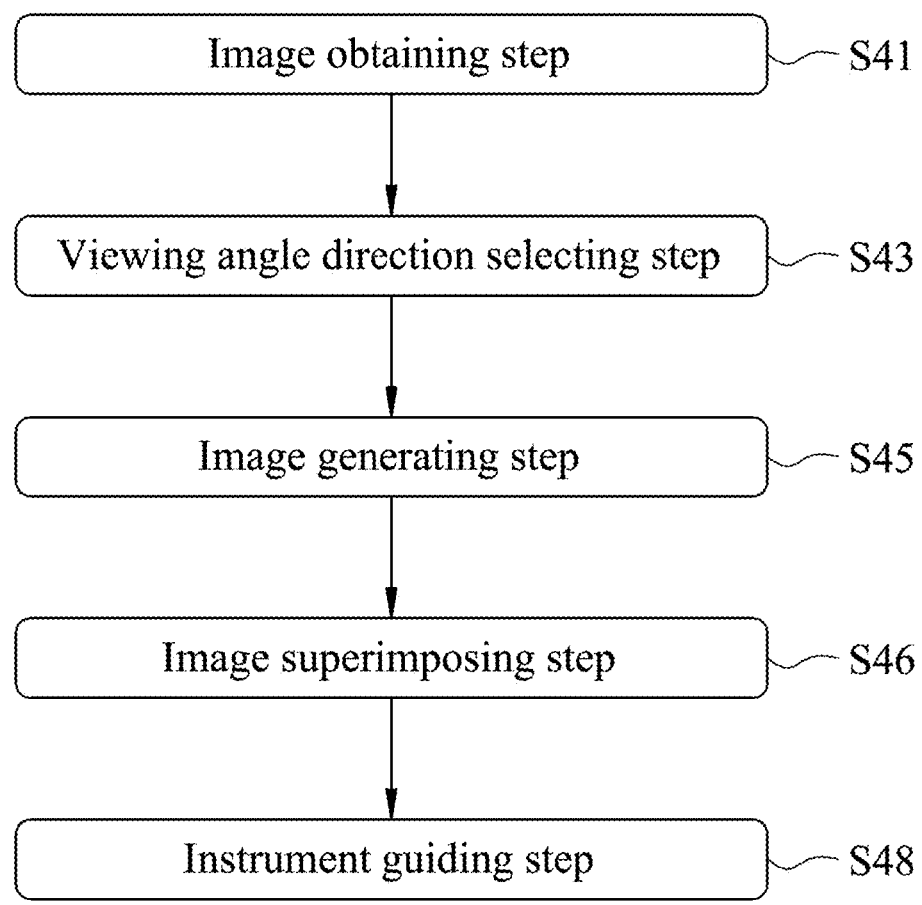
FIG. 8 is a schematic flowchart illustrating a surgical navigation method according to the 4th embodiment of the present disclosure.

FIG. 8 is a schematic flowchart illustrating a surgical navigation method 40 according to the 4th embodiment of the present disclosure. The surgical navigation method 40 of the 4th embodiment is used for guiding a virtual surgical instrument and includes an image obtaining step S41, a viewing angle direction selecting step S43, an image generating step S45, an image superimposing step S46, and an instrument guiding step S48.

In accordance with some embodiments of the present disclosure, the image obtaining step S41 includes obtaining a three-dimensional image (such as, e.g., reading a three-dimensional image of a sacroiliac joint/a SI joint from a memory). The three-dimensional image may be formed by a plurality of two-dimensional original images (e.g., tomographic or cross-sectional images, which can be visualized as virtual slices), and the two-dimensional original images may be generated or obtained through scanning along at least one cutting direction with computed tomography. The three-dimensional image may be a typical three-dimensional data set which is a group of two-dimensional slice images acquired by computed tomography and then stored as a computer-readable file which is able to present internal tissues or organs of a human body on a display.

In accordance with some embodiments, the viewing angle direction selecting step S43 includes selecting a viewing angle direction. In accordance with some embodiments of the present disclosure, the image generating step S45 includes generating one or more two-dimensional images arranged along the viewing angle direction from the three-dimensional image. Respective normal directions of the one or more two-dimensional images are the same as the viewing angle direction, and each of the one or more two-dimensional images is inclined to one of a coronal plane, a sagittal plane and an axial plane. In accordance with some embodiments of the present disclosure, the image superimposing step S46 includes superimposing the one or more two-dimensional images along the viewing angle direction to form a two-dimensional superimposed image, which is inclined to the one of the coronal plane, the sagittal plane and the axial plane.

In accordance with some embodiments of the present disclosure, the instrument guiding step S48 includes guiding a movement of the virtual surgical instrument into the two-dimensional superimposed image, e.g., real time rendering the virtual surgical instrument in the two-dimensional superimposed image according to the position of the surgical instrument. Therefore, the two-dimensional superimposed image of the surgical navigation method 40 is advantageous in distinguishing the position of interest during the surgery. Depending on the viewing angle direction selected, the two-dimensional superimposed image with the proper viewing angle direction inclined to one of the coronal plane, the sagittal plane and the axial plane can be clearly identified in the image allowing for an efficient surgical application, e.g., a biologic fusion surgery of a sacroiliac joint by placing a graft material/an implant therein. Medical staff may correctly plan a surgical path and then implant an instrument, cage and/or graft material in the sacroiliac joint with the two-dimensional superimposed image. It can greatly shorten operation time of finding and determining an implantation position and path, thereby improving safety by reducing the radio exposure and treatment outcomes. The details of the above steps are illustrated in the following 5th and 6th embodiments.

Figure 9:
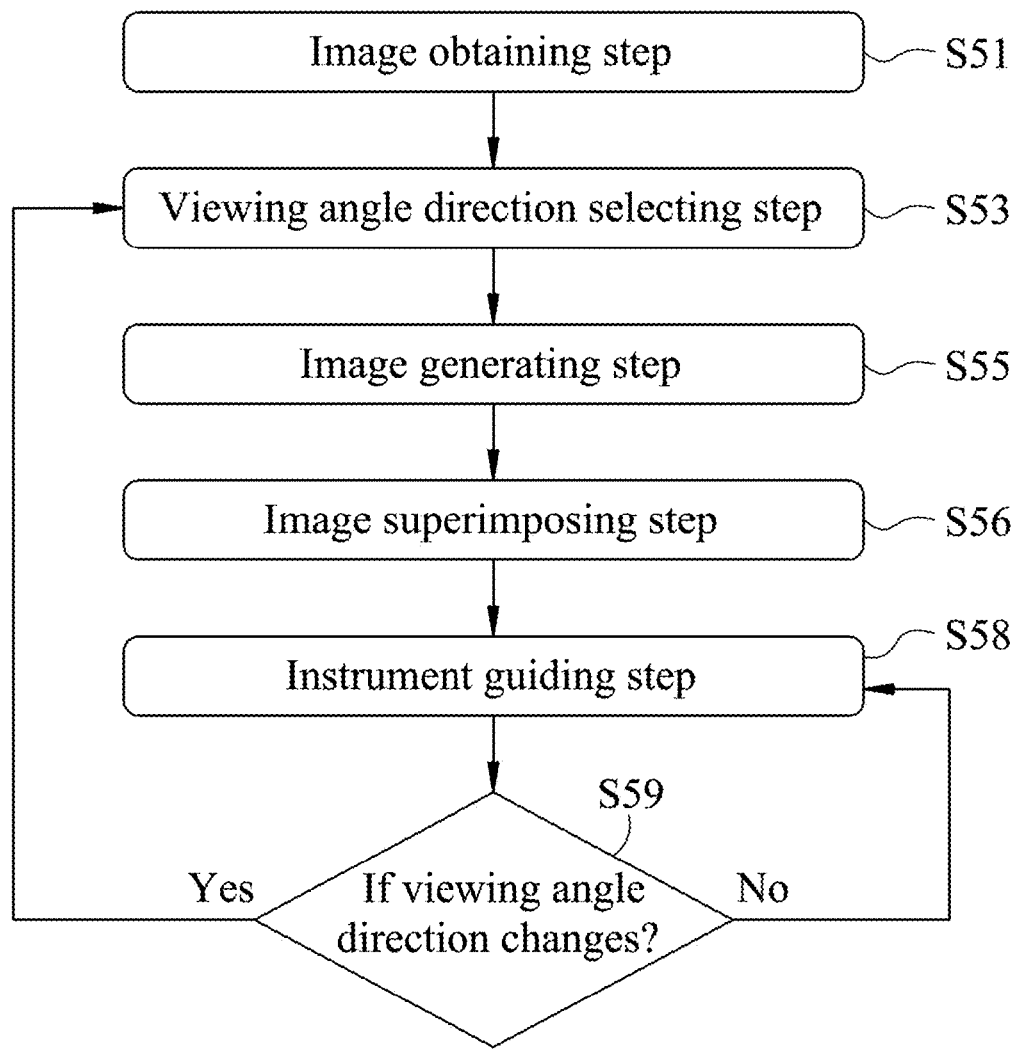
FIG. 9 is a schematic flowchart illustrating a surgical navigation method according to the 5th embodiment of the present disclosure.
Figure 10:
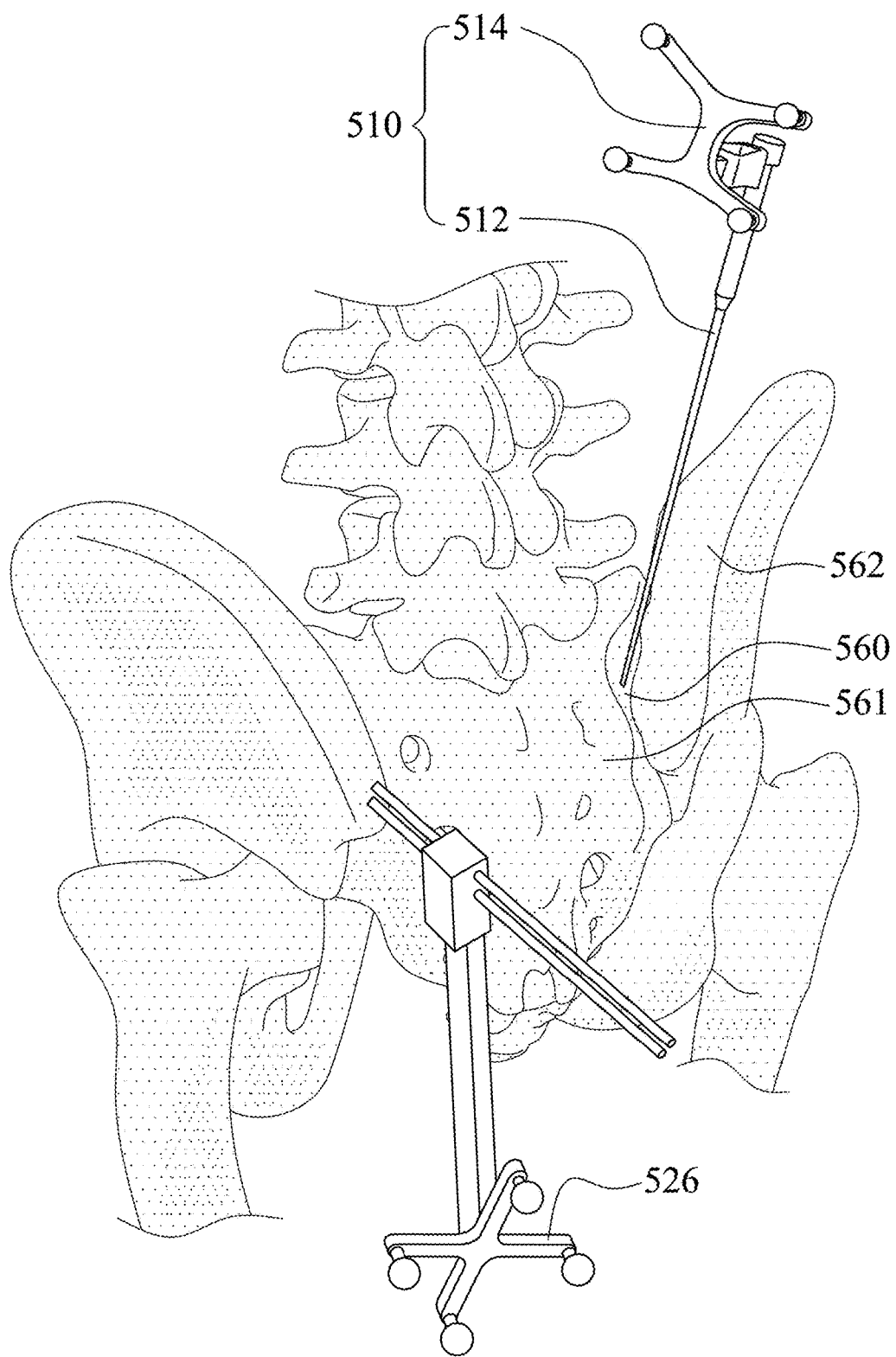
FIG. 10 is a schematic diagram illustrating the guiding of a virtual surgical instrument using the surgical navigation method of FIG. 9.
Figure 11:
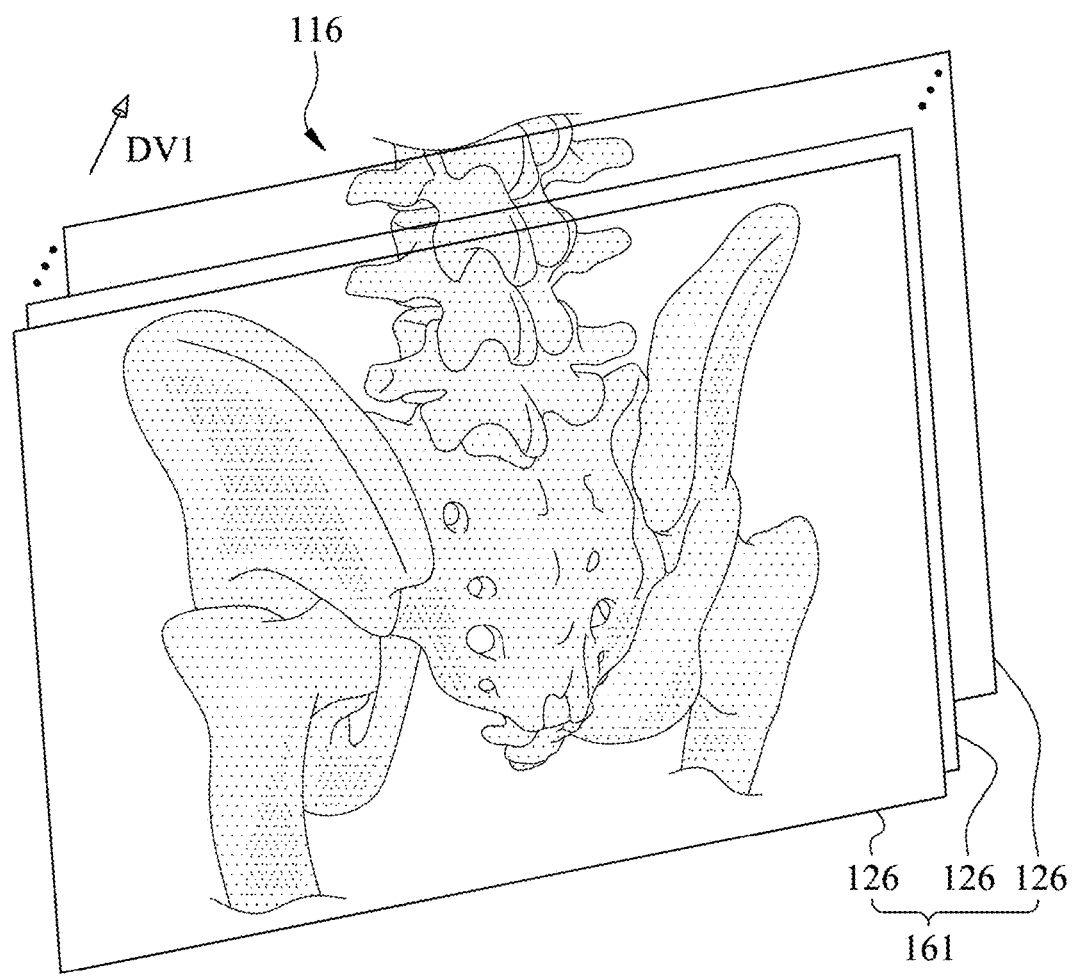
FIG. 11 is a schematic diagram illustrating superimposition of two-dimensional images in an image superimposing step of the surgical navigation method of FIG. 9.
Figure 12:
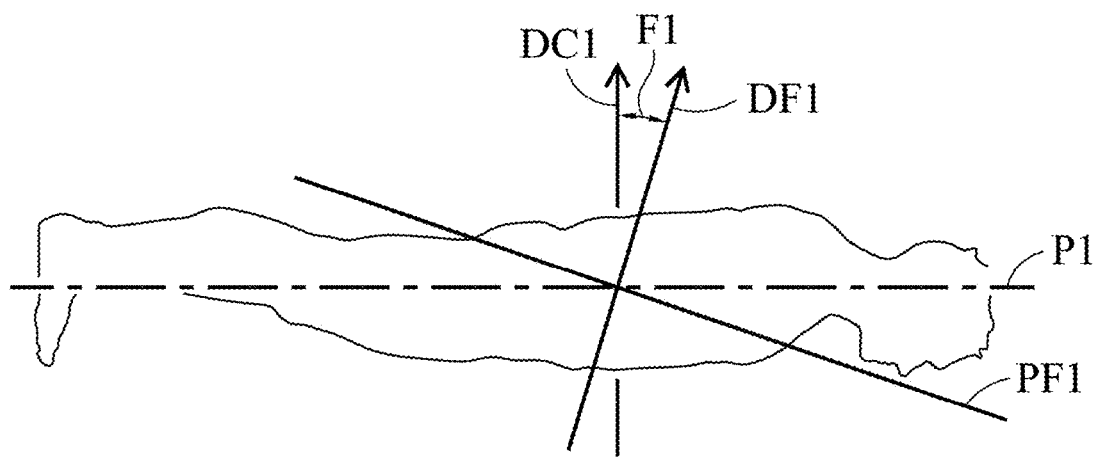
FIG. 12 is a schematic diagram illustrating selection of a first viewing angle direction in a viewing angle direction selecting step of the surgical navigation method of FIG. 9.
Figure 13:
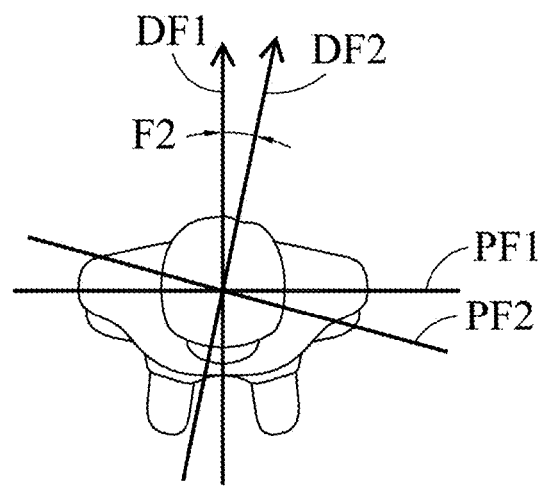
FIG. 13 is a schematic diagram illustrating the selection of the first viewing angle direction continued from FIG. 12.
Figure 14:
FIG. 14 is a schematic diagram illustrating two-dimensional superimposed images in the surgical navigation method of FIG. 9.
Figure 15:
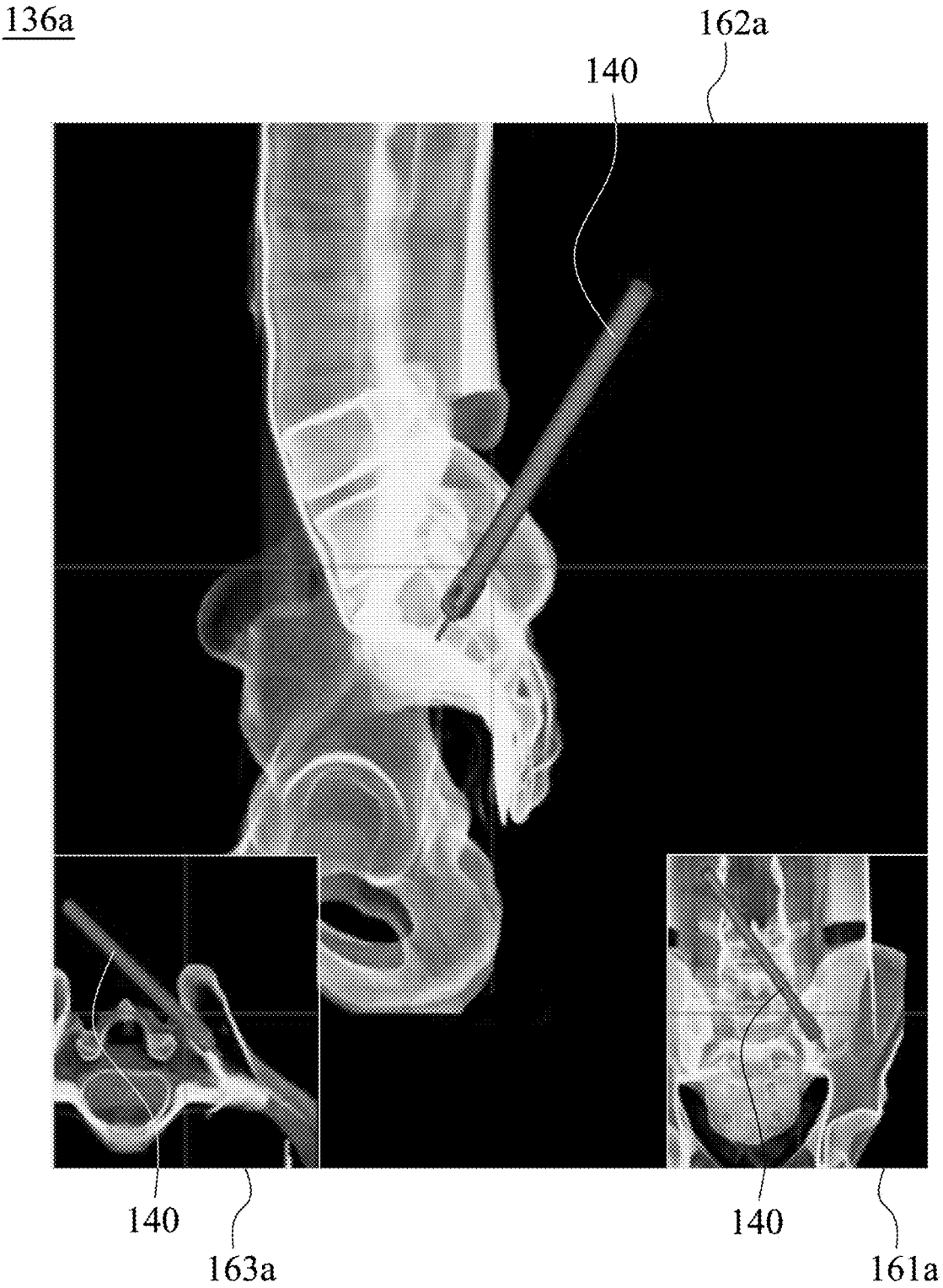
FIG. 15 is a schematic diagram illustrating another two-dimensional superimposed image in the surgical navigation method of FIG. 9.
Figure 16:
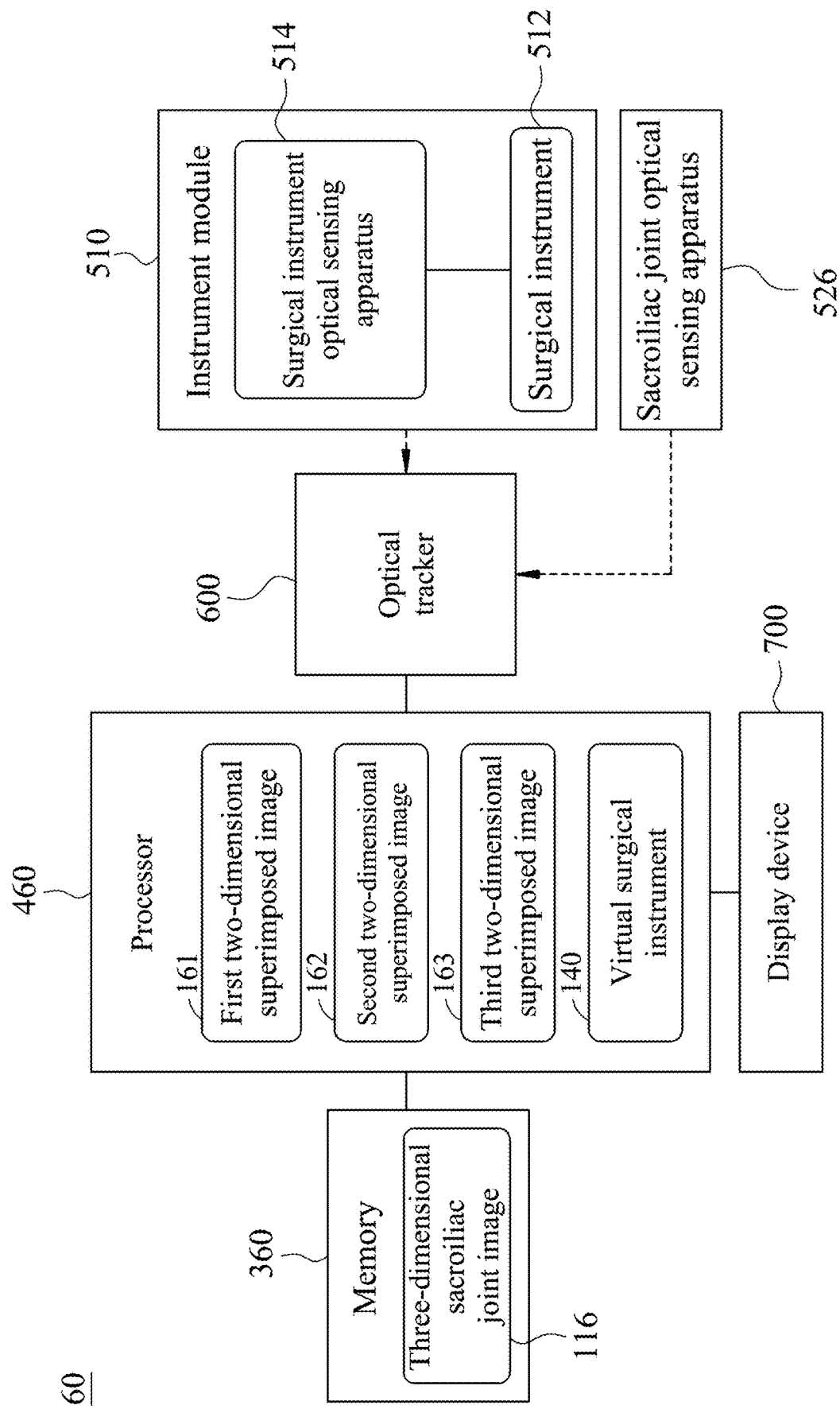
FIG. 16 is a schematic diagram illustrating a surgical navigation system according to the 6th embodiment of the present disclosure.

FIG. 9 is a schematic flowchart illustrating a surgical navigation method 50 according to the 5th embodiment of the present disclosure. FIG. 10 is a schematic diagram illustrating the guiding of a virtual surgical instrument 140 using the surgical navigation method 50 of FIG. 9. FIG. 11 is a schematic diagram illustrating superimposition of two-dimensional images 126 in an image superimposing step S56 of the surgical navigation method 50 of FIG. 9. FIG. 12 is a schematic diagram illustrating selection of a first viewing angle direction DF2 in the viewing angle direction selecting step S53 of the surgical navigation method 50 of FIG. 9. FIG. 13 is a schematic diagram illustrating the selection of the first viewing angle direction DF2 continued from FIG. 12. FIG. 14 is a schematic diagram illustrating a first two-dimensional superimposed image 161, a second two-dimensional superimposed image 162 and a third two-dimensional superimposed image 163 in the surgical navigation method 50 of FIG. 9. FIG. 15 is a schematic diagram illustrating a first two-dimensional superimposed image 161a, a second two-dimensional superimposed image 162a and a third two-dimensional superimposed image 163a in the surgical navigation method 50 of FIG. 9. FIG. 16 is a schematic diagram illustrating a surgical navigation system 60 according to the 6th embodiment of the present disclosure.

The surgical navigation method 50 of the 5th embodiment is used for guiding the virtual surgical instrument 140 and described with an aid of the surgical navigation system 60 shown in FIG. 16 of the 6th embodiment. The virtual surgical instrument 140 may be for example but not limited to a trocar, drill, cage or graft material. The virtual surgical instrument 140 may correspond to one surgical instrument 512 and may be displayed for the surgeon. The surgical navigation method 50 includes an image obtaining step S51, a viewing angle direction selecting step S53, an image generating step S55, an image superimposing step S56, and an instrument guiding step S58. In accordance with some embodiments, the image obtaining step S51, the viewing angle direction selecting step S53, the image generating step S55, the image superimposing step S56, and the instrument guiding step S58 may be applied in conjunction with a biologic fusion technique of the sacroiliac joint 560 by placing a graft material/an implant therein, where the virtual surgical instrument 140 is a virtual sheath, and the surgical instrument 512 is a sheath. However, other virtual surgical instruments and surgical instruments may be used.

In accordance with some embodiments of the present disclosure, the image obtaining step S51 includes obtaining or reading a three-dimensional image of a sacroiliac joint 560 (i.e., a three-dimensional sacroiliac joint image 116) from a memory. The three-dimensional sacroiliac joint image 116 may be formed and constructed by a plurality of two-dimensional original images (e.g., two-dimensional scanned images such as tomographic or cross-sectional images), which may be obtained through scanning along at least one cutting direction such as the direction from the head to the foot of a patient. In accordance with some embodiments, the three-dimensional sacroiliac joint image 116 is a three-dimensional medical image generated through scanning of the sacroiliac joint 560 by CT and reconstruction. During CT scanning, specific scanning parameters are used to obtain a required image. The scanning parameters include a layer thickness and a spacing, where the layer thickness denotes a section thickness of each two-dimensional original image, and the spacing denotes a distance between two adjacent two-dimensional original images. In other words, each two-dimensional original image has a layer thickness, and there is a spacing between adjacent two of the two-dimensional original images.

In accordance with some embodiments of the present disclosure, the viewing angle direction selecting step S53 includes selecting a viewing angle direction, e.g., a first viewing angle direction DV1 shown in FIG. 11, according to an instruction stored in the memory 360 or an instruction input from a user interface. In accordance with some embodiments of the present disclosure, the image generating step S55 includes generating one or more two-dimensional images 126 arranged along the first viewing angle direction DV1 from the three-dimensional sacroiliac joint image 116, and the first viewing angle direction DV1 may be or may not be orthogonal to the cutting direction (the direction of the coronal plane) of the two-dimensional original images during CT scanning.

As shown in FIG. 11, the three-dimensional sacroiliac joint image 116 includes one or more three-dimensional images of a sacrum 561, an ilium 562 and the sacroiliac joint 560, and thereby the two-dimensional images 126 includes one or more two-dimensional images of the sacrum 561, the ilium 562 and the sacroiliac joint 560. Respective normal directions of the one or more two-dimensional images 126 are the same as the first viewing angle direction DV1, and each of the one or more two-dimensional images 126 is inclined to one of the coronal plane, the sagittal plane and the axial plane. In accordance with some embodiments of the present disclosure, the image superimposing step S56 includes superimposing the one or more two-dimensional images 126 along the first viewing angle direction DV1 to form a two-dimensional superimposed image, e.g., the first two-dimensional superimposed image 161 shown in FIG. 14, which is inclined to the one of the coronal plane, the sagittal plane and the axial plane.

In accordance with some embodiments of the present disclosure, for better placing the cage or graft material in the sacroiliac joint 560 for the biologic fusion thereof, the first viewing angle direction DF2 in the viewing angle direction selecting step S53 may be selected or determined as shown in order from FIG. 12 to FIG. 13. First, with reference to FIG. 12, an inclined angle F1 between a normal direction DF1 of a plane PF1 and a normal direction DC1 of a coronal plane P1 of a patient (facing downward in FIG. 12) is selected in a range of 30 degrees to 35 degrees, and an intersection line (i.e., a rotation axis) between the plane PF1 and the coronal plane P1 is parallel to a normal direction of the sagittal plane. Next, with reference to FIG. 13, an inclined angle F2 between the first viewing angle direction DF2 (i.e., a normal direction of a plane PF2) and the normal direction DF1 of the plane PF1 is selected in a range of 20 degrees to 25 degrees, and an intersection line (i.e., a rotation axis) between the plane PF2 and the plane PF1 is parallel to the line representing the plane PF1 shown in FIG. 12. In another embodiment, the intersection line (i.e., a rotation axis) between the plane PF2 and the plane PF1 is parallel to the line representing the coronal plane P1 shown in FIG. 12. In the image generating step S55, one or more two-dimensional images arranged and cut along the first viewing angle direction DF2 from the three-dimensional sacroiliac joint image 116 is generated. In the image superimposing step S56, the one or more two-dimensional images along the first viewing angle direction DF2 are superimposed to form a two-dimensional superimposed image. The one or more two-dimensional images and the two-dimensional superimposed image have the same normal directions as the first viewing angle direction DF2 and are inclined to all the coronal plane P1, the sagittal plane and the axial plane. In other words, there are angles between the two-dimensional superimposed image and the coronal plane P1, the sagittal plane and the axial plane, respectively. The two-dimensional superimposed image is not parallel to any of the coronal plane P1, the sagittal plane and the axial plane.

In accordance with some embodiments of the present disclosure, the instrument guiding step S58 includes guiding a movement of the virtual surgical instrument 140 into first the two-dimensional superimposed image 161 as shown in FIG. 14, e.g., real time rendering the virtual surgical instrument 140 in the first two-dimensional superimposed image 161 according to the position of the surgical instrument 512.

The surgical navigation method 50 can be applied to a biologic fusion surgery of the sacroiliac joint 560. When the surgical navigation method 50 is applied thereto, the surgical instrument 512 is a trocar or drill which is used in the sacroiliac joint 560 for creating an implantation pathway thereof, and the virtual surgical instrument 140 is a virtual sheath, as shown in FIG. 14 and FIG. 13.

In the surgical navigation method 50, the viewing angle direction selecting step S53 may further include selecting or determining a second viewing angle direction, which is orthogonal to the first viewing angle direction DV1; the image generating step S55 may further include generating another one or more two-dimensional images arranged along the second viewing angle direction from the three-dimensional sacroiliac joint image 116, respective normal directions of the another one or more two-dimensional images are the same as the second viewing angle direction, and each of the another one or more two-dimensional images is inclined to another of the coronal plane, the sagittal plane and the axial plane; the image superimposing step S56 may further include superimposing the another one or more two-dimensional images along the second viewing angle direction to form a second two-dimensional superimposed image 162 shown in FIG. 14, which is inclined to the another of the coronal plane, the sagittal plane and the axial plane; and the instrument guiding step S58 may further include guiding the movement of the virtual surgical instrument 140 into the second two-dimensional superimposed image 162.

Furthermore, the viewing angle direction selecting step S53 may further include selecting or determining a third viewing angle direction, which is orthogonal to the first viewing angle direction DV1 and the second viewing angle direction; the image generating step S55 may further include generating further another one or more two-dimensional images arranged along the third viewing angle direction from the three-dimensional sacroiliac joint image 116, and respective normal directions of the further another one or more two-dimensional images are the same as the third viewing angle direction; the image superimposing step S56 may further include superimposing the further another one or more two-dimensional images along the third viewing angle direction to form a third two-dimensional superimposed image 163 shown in FIG. 14; and the instrument guiding step S58 may further include guiding the movement of the virtual surgical instrument 140 into the third two-dimensional superimposed image 163. Furthermore, when the first viewing angle direction is selected, the second and third viewing angle directions may be determined without additional selection of inclined angles with respect to the coronal plane, the sagittal plane or the axial plane, based on pre-determined conditions and the first, second and third viewing angle directions being orthogonal to each other.

In accordance with some embodiments of the present disclosure, the first, second and third viewing angle directions may be selected in order, an inclined angle between the first two-dimensional superimposed image 161 and the coronal plane may be set in a range of 30 degrees to 35 degrees, an inclined angle between the second two-dimensional superimposed image 162 and the sagittal plane may be set in a range of 20 degrees to 25 degrees, and the third two-dimensional superimposed image 163 is orthogonal to each of the first two-dimensional superimposed image 161 and the second two-dimensional superimposed image 162. With reference to FIG. 11, the normal direction of the first two-dimensional superimposed image 161 (i.e., the first viewing angle direction DV1) and a normal direction of the coronal plane may be the same or different. An inclined angle between the normal direction of the first two-dimensional superimposed image 161 (i.e., the first viewing angle direction DV1) and the normal direction of the coronal plane is in the range of 30 degrees to 35 degrees, that is, the inclined angle between the first two-dimensional superimposed image 161 and the coronal plane is in the range of 30 degrees to 35 degrees. Specifically, an intersection line between the first two-dimensional superimposed image 161 and the coronal plane is parallel to a normal direction of the axial plane, as shown in FIG. 11. In accordance with some embodiments of the present disclosure, the surgical navigation method is not limited for placing the graft material in the sacroiliac joint. It should be understood that any of first, second and third two-dimensional superimposed images can be denominated to have an inclined angle with respect to and correspond to any of a coronal plane, a sagittal plane and an axial plane, and when any two of the first, second and third viewing angle directions are selected, the last one thereof can be determined based on the first, second and third viewing angle directions being orthogonal to each other.

Moreover, the first two-dimensional superimposed image 161, the second two-dimensional superimposed image 162 and the third two-dimensional superimposed image 163 can be displayed on a display device 700, as shown in FIG. 14.

Comparing to the conventional biologic fusion surgery of the sacroiliac joint, the surgery proceeded only with an aid of a two-dimensional captured image is hard to determine the position for placing a graft material. However, the biologic fusion surgery of the sacroiliac joint 560 with an aid of the surgical navigation method 50 according to the present disclosure is advantageous in more accurately determine the pathway and/or position (e.g., the position of a teardrop superimposed image 169 in the first two-dimensional superimposed image 161 shown in FIG. 12) for docking, drilling, and placing the cage and/or graft material in the sacroiliac joint 560 by the surgical instrument 512.

With reference to FIG. 9, FIG. 14 and FIG. 15, the surgical navigation method 50 may further include a step S59. In the step S59, if any of the first viewing angle direction DV1, the second viewing angle direction and the third viewing angle direction corresponding to FIG. 12 is required to be changed for more assisting the surgery of placing the graft material in the sacroiliac joint 560, it is determined to return to the viewing angle direction selecting step S53 for selecting another set of the first, second and third viewing angle directions, which are orthogonal to each other. Next, the image generating step S55 and the image superimposing step S56 are performed to form the first two-dimensional superimposed image 161a, the second two-dimensional superimposed image 162a and the third two-dimensional superimposed image 163a, as shown in FIG. 15. For example, the first, second and third viewing angle directions respectively corresponding to the first two-dimensional superimposed image 161a, the second two-dimensional superimposed image 162a and the third two-dimensional superimposed image 163a shown in FIG. 15 can be selected according to the previous first two-dimensional superimposed image 161, the previous second two-dimensional superimposed image 162 and the previous third two-dimensional superimposed image 163 shown in FIG. 14, displayed on the display device 700. In the step S59, if it is not required, it is determined to stay in the instrument guiding step S58 to continue to cooperate by the instrument module 510, the sacroiliac joint optical sensing apparatus 526 and the virtual surgical instrument 140.

With reference to FIG. 16, the surgical navigation system 60 according to the 6th embodiment of the present disclosure is configured to guide the virtual surgical instrument 140 and includes a memory 360, a processor 460, an instrument module 510, a sacroiliac joint optical sensing apparatus 526, an optical tracker 600, and a display device 700.

Although not shown, the various components of the surgical navigation system 60 need not be fully contained within the user device/equipment. Each of the components may be physically separated from another and more than one of the components may be used to perform methods consistent with the present disclosure. Even though the components may be physically separated, the components may still be communicably connected by means of wired or wireless technology. For example, different components of the surgical navigation system 60 and user device may be connected through the Internet, a LAN (local area network), a WAN (wide area network), databases, servers, RF (radio frequency) signals, cellular technology, Ethernet, telephone, "TCP/IP" (transmission control protocol/internet protocol), and any other electronic communication format.

In accordance with some embodiments of the present disclosure, the memory 360 is configured to store and access the three-dimensional sacroiliac joint image 116, where the three-dimensional sacroiliac joint image 116 is a three-dimensional medical image formed by the two-dimensional original images through scanning of the sacroiliac joint 560 by CT, and the two-dimensional original images are obtained through scanning along at least one cutting direction. The memory 360 may include any form of computer-readable storage mediums such as non-volatile or volatile memories including, by way of example, semiconductor memory devices, such as EPROM, RAM, ROM, DRAM, EEPROM, and flash memory devices; magnetic disks such as internal hard disks and removable disks; magneto-optical disks; DVD disks, and CD-ROM disks. Memory 360 may be used to store instructions or commands of program codes.

In accordance with some embodiments of the present disclosure, the processor 460 (i.e., a controller, a computing processing apparatus, etc.) is electrically connected to the memory 360, where the processor 460 receives the three-dimensional sacroiliac joint image 116 and is configured to perform operations including the following steps: the image obtaining step S41/S51, the viewing angle direction selecting step S43/S53, the image generating step S45/S55, the image superimposing step S46/S56, and the instrument guiding step S48/S58 of the 4th/5th embodiment described above and shown in FIG. 8 to FIG. 15.

In accordance with some embodiments of the present disclosure, the instrument module 510 includes the surgical instrument 512 and the surgical instrument optical sensing apparatus 514, where the surgical instrument 512 is controlled and displaced by medical staff. The surgical instrument optical sensing apparatus 514 may be disposed on the surgical instrument 512, and includes a reflective ball and a fixing frame, and the fixing frame may be located between the reflective ball and the surgical instrument 512. The surgical instrument 512 may be a sheath or another surgical instrument, depending on the selection of medical staff and use conditions. The sacroiliac joint optical sensing apparatus 526 may be disposed around the sacroiliac joint 560 and includes a reflective ball and a fixing frame. The fixing frame may be located between the reflective ball and the sacroiliac joint 560.

The optical tracker 600 may be electrically connected to the processor 460 and configured to track the sacroiliac joint 560 and the surgical instrument 512 around an anatomical region of a patient, and assist to enhance the accuracy of the virtual surgical instrument 140. When the medical staff controls the surgical instrument 512, the surgical instrument optical sensing apparatus 514 may be facing to the optical tracker 600, so that the optical tracker 600 can track the surgical instrument 512 in real time. In addition, the sacroiliac joint optical sensing apparatus 526 may also be facing to the optical tracker 600, so that the optical tracker 600 can track the sacroiliac joint 560 in real time. In detail, the processor 460 is further configured to receive a surgical instrument tracking signal and an anatomical region tracking signal from the optical tracker 600; and send instructions to the display device 700 to display the virtual surgical instrument 140 on the first two-dimensional superimposed image 161/161a, the second two-dimensional superimposed image 162/162a and the third two-dimensional superimposed image 163/163a shown in FIG. 14/15, the virtual surgical instrument 140 positioned and oriented with respect to the anatomical region in a manner corresponding to a position and orientation of the surgical instrument 512 with respect to the anatomical region.

In accordance with some embodiments of the present disclosure, the display device 700 may be electrically connected to the processor 460, and displays a screen picture, and the screen picture presents a set of the first two-dimensional superimposed image 161, the second two-dimensional superimposed image 162 and the third two-dimensional superimposed image 163 shown in FIG. 12, or another set of the first two-dimensional superimposed image 161a, the second two-dimensional superimposed image 162a and the third two-dimensional superimposed image 163a shown in FIG. 13, or any set of the first, second and third two-dimensional superimposed images orthogonal to each other. The display device 700 may be any conventional user interface display device. For example, the display device 700 may include computer monitors, televisions, and LCD displays. The display device 700 may display GUI which allows a user to interact with the hardware and software applications of the surgical navigation system 60.

Although the present disclosure has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A surgical navigation method comprising steps of:
   obtaining a three-dimensional image;
   selecting a viewing angle direction;
   generating one or more two-dimensional images arranged along the viewing angle direction from the three-dimensional image;
   superimposing the one or more two-dimensional images along the viewing angle direction to form a two-dimensional superimposed image; and
   guiding a movement of a virtual surgical instrument into the two-dimensional superimposed image;
   wherein the two-dimensional superimposed image presents at least one two-dimensional superimposed region according to the viewing angle direction;
   wherein the surgical navigation method further comprises adjusting the one or more two-dimensional images superimposed along the viewing angle direction according to a contour sharpness of the at least one two-dimensional superimposed region in the two-dimensional superimposed image;
   wherein the two-dimensional superimposed image is a first two-dimensional superimposed image, the viewing angle direction is a first viewing angle direction, and the surgical navigation method further comprises:
     selecting a second viewing angle direction, which is different from the first viewing angle direction;
     generating another one or more two-dimensional images arranged along the second viewing angle direction from the three-dimensional image;
     superimposing the another one or more two-dimensional images along the second viewing angle direction to form a second two-dimensional superimposed image; and
     guiding the movement of the virtual surgical instrument into the second two-dimensional superimposed image.

2. The surgical navigation method of claim 1, wherein the three-dimensional image is a computed tomography scan.

3. The surgical navigation method of claim 1, wherein the one or more two-dimensional images include one or more images of a sacrum, an ilium and a sacroiliac joint.

4. The surgical navigation method of claim 1, wherein respective normal directions of the one or more two-dimensional images are the same as the viewing angle direction.

5. The surgical navigation method of claim 4, wherein each of the one or more two-dimensional images is inclined to one of a sagittal plane, a coronal plane and an axial plane, and the two-dimensional superimposed image is inclined to the one of the sagittal plane, the coronal plane and the axial plane.

6. The surgical navigation method of claim 5, wherein
the second viewing angle direction is orthogonal to the first viewing angle direction;
wherein respective normal directions of the another one or more two-dimensional images are the same as the second viewing angle direction, and each of the another one or more two-dimensional images is inclined to another of the sagittal plane, the coronal plane and the axial plane;
wherein the second two-dimensional superimposed image is inclined to the another of the coronal plane, the sagittal plane and the axial plane.

7. The surgical navigation method of claim 6, further comprising:
selecting a third viewing angle direction, which is orthogonal to the first viewing angle direction and the second viewing angle direction;
generating further another one or more two-dimensional images arranged along the third viewing angle direction from the three-dimensional image, wherein respective normal directions of the further another one or more two-dimensional images are the same as the third viewing angle direction;
superimposing the further another one or more two-dimensional images along the third viewing angle direction to form a third two-dimensional superimposed image; and
guiding the movement of the virtual surgical instrument into the third two-dimensional superimposed image.

8. The surgical navigation method of claim 7, wherein an inclined angle between the first two-dimensional superimposed image and the coronal plane is in a range of 30 degrees to 35 degrees.

9. The surgical navigation method of claim 8, wherein an inclined angle between the second two-dimensional superimposed image and the sagittal plane is in a range of 20 degrees to 25 degrees.

10. The surgical navigation method of claim 7, wherein the first, second, and/or third two-dimensional superimposed images are displayed on a display device.

11. The surgical navigation method of claim 10, wherein the first, second and third viewing angle directions are selected according to a previous first two-dimensional superimposed image, a previous second two-dimensional superimposed image, and a previous third two-dimensional superimposed image displayed on the display device.

12. A surgical navigation system, comprising:
a memory configured to store a three-dimensional image;
a controller configured to:
select a viewing angle direction according to an instruction;
generate one or more two-dimensional images arranged along the viewing angle direction from the three-dimensional image;
superimpose the one or more two-dimensional images along the viewing angle direction to form a two-dimensional superimposed image; and
guide a virtual surgical instrument into the two-dimensional superimposed image; and
a display device configured to display the two-dimensional superimposed image;
wherein the two-dimensional superimposed image presents at least one two-dimensional superimposed region according to the viewing angle direction;
wherein the controller is configured to adjust the one or more two-dimensional images superimposed along the viewing angle direction according to a contour sharpness of the at least one two-dimensional superimposed region in the two-dimensional superimposed image;
wherein the two-dimensional superimposed image is a first two-dimensional superimposed image, the viewing angle direction is a first viewing angle direction, and the controller is further configured to:
select a second viewing angle direction according to the instruction, wherein the second viewing angle direction is different from the first viewing angle direction;
generate another one or more two-dimensional images arranged along the second viewing angle direction from the three-dimensional image;
superimpose the another one or more two-dimensional images along the second viewing angle direction to form a second two-dimensional superimposed image; and
guide the virtual surgical instrument into the second two-dimensional superimposed image.

13. The surgical navigation system of claim 12, wherein the two-dimensional superimposed image includes one or more images of a sacrum, an ilium and a sacroiliac joint.

14. The surgical navigation system of claim 12, wherein respective normal directions of the one or more two-dimensional images are the same as the viewing angle direction.

15. The surgical navigation system of claim 14, wherein each of the one or more two-dimensional images is inclined to one of a coronal plane, a sagittal plane and an axial plane, and the two-dimensional superimposed image is inclined to the one of the coronal plane, the sagittal plane and the axial plane.

16. The surgical navigation system of claim 15, wherein
the second viewing angle direction is orthogonal to the first viewing angle direction;
wherein respective normal directions of the another one or more two-dimensional images are the same as the second viewing angle direction, and each of the another one or more two-dimensional images is inclined to another of the coronal plane, the sagittal plane and the axial plane;
wherein the second two-dimensional superimposed image is inclined to the another of the coronal plane, the sagittal plane and the axial plane.

17. The surgical navigation system of claim 16, wherein the controller is further configured to:
select a third viewing angle direction, which is orthogonal to the first viewing angle direction and the second viewing angle direction;
generate further another one or more two-dimensional images arranged along the third viewing angle direction from the three-dimensional image, wherein respective normal directions of the further another one or more two-dimensional images are the same as the third viewing angle direction;

superimpose the further another one or more two-dimensional images along the third viewing angle direction to form a third two-dimensional superimposed image; and guide the virtual surgical instrument into the third two-dimensional superimposed image.

18. The surgical navigation system of claim 17, wherein an inclined angle between the first two-dimensional superimposed image and the coronal plane is in a range of 30 degrees to 35 degrees.

19. The surgical navigation system of claim 18, wherein an inclined angle between the second two-dimensional superimposed image and the sagittal plane is in a range of 20 degrees to 25 degrees.

20. The surgical navigation system of claim 17, wherein the display device simultaneously displays the first, second, and/or third two-dimensional superimposed images.

21. The surgical navigation system of claim 20, wherein the instruction of the first, second and third viewing angle directions are provided according to a previous first two-dimensional superimposed image, a previous second two-dimensional superimposed image, and a previous third two-dimensional superimposed image displayed on the display device.

22. The surgical navigation system of claim 12, further comprising:
    an optical tracker configured to track the virtual surgical instrument and an anatomical region of a patient;
    wherein the controller is further configured to:
    receive a surgical instrument tracking signal and an anatomical region tracking signal from the optical tracker; and
    send instructions to the display device to display the virtual surgical instrument on the two-dimensional superimposed image, the virtual surgical instrument positioned and oriented with respect to the anatomical region in a manner corresponding to a position and orientation of a surgical instrument with respect to the anatomical region.

23. A non-transitory computer-readable storage medium, comprising instructions, which when executed on a processor causes the processor to perform a surgical navigational method, the surgical navigational method comprising steps of:
    obtaining a three-dimensional image;
    selecting a viewing angle direction according to an instruction;
    generating one or more two-dimensional images arranged along the viewing angle direction from the three-dimensional image;
    superimposing the two-dimensional images along the viewing angle direction to form a two-dimensional superimposed image; and
    guiding a movement of a virtual surgical instrument into the two-dimensional superimposed image;
    wherein the two-dimensional superimposed image presents at least one two-dimensional superimposed region according to the viewing angle direction;
    wherein the surgical navigation method further comprises adjusting the one or more two-dimensional images superimposed along the viewing angle direction according to a contour sharpness of the at least one two-dimensional superimposed region in the two-dimensional superimposed image;
    wherein the two-dimensional superimposed image is a first two-dimensional superimposed image, the viewing angle direction is a first viewing angle direction, and the surgical navigation method further comprises:
    selecting a second viewing angle direction, which is different from the first viewing angle direction;
    generating another one or more two-dimensional images arranged along the second viewing angle direction from the three-dimensional image;
    superimposing the another one or more two-dimensional images along the second viewing angle direction to form a second two-dimensional superimposed image; and
    guiding the movement of the virtual surgical instrument into the second two-dimensional superimposed image.

* * * * *